(12) United States Patent
Ueck

(10) Patent No.: US 6,800,305 B1
(45) Date of Patent: Oct. 5, 2004

(54) PHARMACEUTICAL COMPOSITION THAT CONTAINS EUCALYPTUS AND ORANGE OIL

(75) Inventor: Henning Ueck, Bekmunde (DE)

(73) Assignee: Akh Arzneimittelkontor GmbH, Bekmunde (DE)

( * ) Notice: Subject to any disclaimer, the term of this patent is extended or adjusted under 35 U.S.C. 154(b) by 164 days.

(21) Appl. No.: 10/088,469

(22) PCT Filed: Sep. 12, 2000

(86) PCT No.: PCT/EP00/08903
§ 371 (c)(1),
(2), (4) Date: Mar. 15, 2002

(87) PCT Pub. No.: WO01/19382
PCT Pub. Date: Mar. 22, 2001

(30) Foreign Application Priority Data

Sep. 16, 1999 (DE) ..................... 299 16 014 U

(51) Int. Cl.⁷ .................. A01N 15/00; A61K 35/78
(52) U.S. Cl. ..................... 424/736; 424/742
(58) Field of Search ................. 424/736, 742

(56) References Cited

U.S. PATENT DOCUMENTS

| 4,713,291 A | * | 12/1987 | Sasaki et al. ............... 428/373 |
| 5,466,719 A | * | 11/1995 | Jakobson et al. ............ 514/785 |
| 5,686,074 A | * | 11/1997 | Stewart .................... 424/195.1 |
| 6,419,904 B1 | * | 7/2002 | Combe et al. ................ 424/49 |
| 6,444,238 B1 | * | 9/2002 | Weise ....................... 4424/736 |
| 6,495,177 B1 | * | 12/2002 | Devries et al. ............. 424/441 |

FOREIGN PATENT DOCUMENTS

| CH | 688787 | * | 3/1988 |
| CH | 688787 | * | 3/1998 |

OTHER PUBLICATIONS

Computer CAPLUS Abstract 1992:557449 Ishii et al JP 04159212 Jan. 1990.*

Computer CAPLUS Abstract 1979:409357 Sato et al JP 54026339 Jul. 1977.*

Derewent Abstract 1996–114540 Dubinskii Abstract RU2038092 Published Jun. 27, 1995.*

* cited by examiner

Primary Examiner—Herbert J. Lilling
(74) Attorney, Agent, or Firm—Schweitzer Cornman Gross & Bondell LLP

(57) ABSTRACT

The invention relates to a pharmaceutical composition comprising eucalyptus oil and orange oil in combined form, which can be used, preferably, for the treatment of diseases of the respiratory tract, which are caused by microorganisms.

13 Claims, No Drawings

PHARMACEUTICAL COMPOSITION THAT CONTAINS EUCALYPTUS AND ORANGE OIL

The invention relates to a pharmaceutical composition comprising eucalyptus oil and orange oil in combined form, which can be used, preferably, for the treatment of diseases of the respiratory tract, which are caused by microorganisms.

An uncomplicated bronchitis is defined as an inflammatory disease of the lower respiratory tract and represents one of the diseases, which are diagnosed most frequently by physicians. Exposure to cold and wet conditions in the cooler time of the year frequently prepare the path for bronchitis, which is transferred from person to person by droplet infection. Correspondingly, epidemics occur frequently. A series of viruses, such as influenza viruses, parainfluenza viruses, rhino viruses, REO viruses, coxsackie viruses, ECHO viruses and adeno viruses come into consideration as causative organisms. The origin is hardly ever primarily bacterial. However, bacterial superinfections with Haemophilus influenzae, Streptococcus pneumoniae and less frequently also staphylococci may be superimposed on viral infections.

At the start of the disease, the mucus membrane of the central respiratory tract is reddened and edematous. Polymorphonuclear granulocytes and lymphocytes infiltrate the mucous membranes. Mucoserous secretion is found increasingly in the bronchial lumen. After granulocytes have migrated into the mucus, the latter becomes purulent. In the further course of the disease, large areas of the bronchial ciliated epithelium perish and are rejected into the bronchial lumen. This stage of ulcerative bronchitis is predisposed to bacterial superinfection.

In the next phase, over a few days, a dry cough in association with pain behind the sternum occur as clinical symptoms. After that, the cough becomes productive.

The color of the sputum is gray to yellow and the pain of coughing disappears. Coughing and sputum can last for two to three weeks. A causal treatment of the viral infection is not possible. A bacterial superinfection can be treated with antibiotics.

If a bacterial superinfection is suspected in the course of the acute bronchitis, an antibiotic treatment with cephalosporins of the second and third generation or with macrolide antibiotics of the newer generation is indicated.

Because of the primarily viral origin of the acute syndrome, the value of treating acute bronchitis immediately with antibiotics is a very controversial subject, especially if the progressing development of resistance by the bacteria, as well as economic points of view, are taken into consideration. Until now, the value of antibiotics for the indication of "acute bronchitis" could not be confirmed by means of randomized, placebo-controlled studies with antibiotics.

In spite of this controversy, it is estimated that, in practice, antibiotics are prescribed for more than 65% of the patients with the diagnosis of acute bronchitis.

Under practical conditions, however, an exact diagnosis is frequently not made, so that antibiotics are used even when they are not needed therapeutically. The uncritical use of antibiotics has resulted in an increase in resistance to them by an increasing number of bacteria. This increase in resistance depends on the frequency of use. Antibiotics result in a selection pressure, which favors the growth of resistant sins of bacteria.

For example, strains of staphylococci with a reduced resistance to vancomycin have meanwhile also occurred. This is dramatic, because this antibiotic previously has been used as the last means for combating bacterial strains, which are resistant to the antibiotics commonly used.

In this situation, there is a need for an alternative treatment.

It is therefore an object of the present invention to indicate a pharmaceutical composition, which is equivalent therapeutically to the previously used antibiotics, has a few side effects and does not promote the development of resistance.

This objective is accomplished by the distinguishing features of the independent claims. The dependent claims define advantageous embodiments of the invention.

Surprisingly, it was found that a combination of orange oil and eucalyptus oil, preferably in a ratio of 2:1, not only was significantly superior to placebo in a clinical test, but also was equivalent to an antibiotic treatment.

In a double blind, randomized, and placebo-controlled clinical study of patients with acute bronchitis, the effectiveness and compatibility of a 14-day treatment with Eucalyptus oil/orange oil was investigated. A parallel group of patients was treated for 14 days correspondingly with placebo or cefuroxime.

The treatment groups comprised 170 patients with Eucalyptus oil/orange oil, 172 patients with placebo and 171 patients with cefuroxime.

The superiority of Eucalyptus oil/orange oil over placebo was found to be statistically significant on the basis of terminations of the investigation because of a worsening of the acute bronchitis after 7±2 treatment days. On a percentage basis, 7.1 percent of the patients treated with Eucalyptus oil/orange oil, 22.7 percent of the patients treated with placebo and 7.6 percent of the patients treated with cefuroxime experienced a worsening of the symptoms.

Even after 14±2 treatment days, there was still a worsening of the acute bronchitis. This affected only 1.8 percent of the patients in the Eucalyptus oil/orange oil group, a number which differed clearly from the 36.6 percent of patients in the placebo group. In the cefuroxime group, 16.4 percent of the patients were affected, that is, 10 times as many patients as in the Eucalyptus oil/orange oil group.

As a further indication of the success of the treatment, there was still a pathological ausculatory finding after 7±2 treatment days in 27.1 percent of the patients treated with Eucalyptus oil/orange oil in comparison to 48.3 percent of the placebo patients. In the cefuroxime group, 26.3 percent still had a pathological ausculatory finding. After 14±2 days, the percentage of patients in the Eucalyptus oil/orange oil group was reduced to 2.9 percent; on the other hand, in the placebo group, 14.5 percent of the patients still showed pathological respiratory sounds. For the patients treated with cefuroxime, the percentage at 7.6 percent was also higher than in the Eucalyptus oil/orange oil group. The observed hypersensitivity of the bronchial system, which was observed in about 50 percent of all patients during a first visit, was clearly low after 7±2 treatment days in patients treated with Eucalyptus oil/orange oil than in the placebo group. With respect to the nighttime attacks of coughing, which affect night rest, there was a clear decrease from day 5 of the treatment onward in the two treatment groups in comparison to the placebo group. The difference in the absence of coughing attacks during the day between the three treatment groups and the placebo group became clear only after nine days of treatment. After a 14-day treatment, half of the Eucalyptus oil/orange oil patients and only 30 percent of the placebo patients no longer coughed. The effectiveness of Eucalyptus oil/orange oil was rated to be significantly better by physicians and patients after 7±2 and 14±2 days and was also superior to that of cefuroxime. Likewise, from the fourth day of the treatment onward, the general state of health of the patients treated with Eucalyptus oil/orange oil was clearly better than that of patients of the placebo group. In the evaluation of the general state of health, there were no differences worth mentioning between the Eucalyptus oil/orange oil group and the cefuroxime group.

With regard to the safety and compatibility of the medications of the study, there were no relevant differences between the treatment groups and between the final visit and the first visit according to a physical examination and the determination of laboratory and vital parameters. This conclusion also applies to the member and evaluation of the undesirable events, which occurred, and therefore emphasizes the good compatibility of Eucalyptus oil/orange oil.

In 93 percent of the patients, the administration of Eucalyptus oil/orange oil in the case of acute bronchitis prevented a worsening of the syndrome in comparison to the administration of placebo and therefore led to a more rapid complete cure. It is frequently the practice to administer antibiotics immediately in the case of acute bronchitis. Such a treatment was not superior to a treatment with Eucalyptus oil/orange oil. The prompt use of antibiotics for this indication should therefore be reviewed carefully for economic reasons as well as because of the danger of developing resistance.

The above clinical study shows that the combination of Eucalyptus oil/orange oil is outstandingly suitable for the treatment of the infectious diseases and inflammation of the respiratory passages.

The inventive combinations of Eucalyptus oil/orange oil can be administered subcutaneously, intramuscularly, intravenously, topically and preferably orally. Pursuant to the invention, Eucalyptus oil/orange all preferably is used in the form of soft or hard gelatin capsules or in liquid or semi-solid forms of administration. The oil may also be used in pure form or in combination with other biologically active materials, such as menthol and conventional inactive ingredients. Moreover, it can be combined with conventional inactive ingredients for the treatment of an existing basic disease, for example, with nitrates for the treatment of cardiac diseases.

Sulubilizers are preferred as inactive ingredients. As such, organic solutions, preferably ethanol, surfactants, preferably sodium dodecyl sulfate or sodium desoxycholate, carbohydrates, preferably glucose or dextrose, or lipids, preferably phosphatidylcholine, as well as mixtures of these materials can be used. These solubilizers usually are employed in amounts of 0.1 to 20 percent by weight and preferably of 0.2 to 15 percent by weight, based on the amount of Eucalyptus oil/orange oil. In accordance with the invention, the weight ratio of Eucalyptus oil to orange oil may be between 1:10 and 10:1, with a preferred ratio being 2:1. The weight content of Eucalyptus oil/orange oil may be from 1–80%, preferably 10–75%, and more preferably 40–70%.

In the case of hard or soft gelatin capsules, for example, the content of Eucalyptus oil/orange oil preferably ranges from 1 to 80 percent by weight, especially from 16 to 40 percent by weight and particularly from 20 to 35 percent by weight. One capsule preferably contains 40 to 350 mg and particularly 100 to 300 mg of Eucalyptus oil/orange oil. The daily dose is of the order of 0.01 to 0.2 g of Eucalyptus oil/orange oil per kilogram of body weight.

The orange oil, used pursuant to the invention, preferably contains predominantly limonene, especially (+)-limonene, that is, at least 90 percent by weight, preferably at least 93 percent by weight and particularly between 93 and 98 percent by weight of the total amount of orange oil. The Eucalyptus oil preferably is used in the form of a rectified essential oil, which preferably contains more than 70 percent of 1,8-cineol, as well as α-pinene, preferably (+)-α-pinene.

The oil preferably is used as a solution in a neutral oil or a natural fatty oil. Coconut oil, rapeseed oil and corn oil are suitable as natural oils. Medium chain length (C6–C12) triglycerides, especially caprylic and capric triglycerides, such as Miglyol 810 (molecular weight of about 520; gas chromatographic composition: C6 max. 2%; C8 65–75%; C10 25–35%, C12 max. 2%) and Miglyol 812 (molecular weight of about 520; gas chromatographic composition: C6 max. 3%; C8 50–65%; C10 30–45%, C12 max. 5%) are preferred neutral oils.

The concentration of Eucalyptus oil/orange oil in a solution, which is to be taken orally, preferably ranges from 5 to 30 g/L, especially from 10 to 20 g/L and particularly from 12 to 18 g/L.

Preferred liquid forms of administration are syrups and emulsions, the composition of which, according to Examples 1 and 2, may be as follows:

EXAMPLE 1

Syrup Containing Eucalyptus Oil/orange oil

| Component | Content (% by weight |
|---|---|
| Macrogol glycerol hydroxystearate | 6–8 |
| Eucalyptus oil/orange oil | 0.5–3.0 |
| xylitol | 18–22 |
| carrageenan | 0.4–0.6 |
| trisodium citrate dihydrate | 0.05–0.1 |
| potassium sorbate | 0.1–0.2 |
| Macrogol 1500 | 8–10 |
| honey aroma | 0.1–0.2 |
| citric acid | 0.1–0.2 |
| aqua purificata | to 100% |

EXAMPLE 2

Emulsion Containing Eucalyptus Oil and Orange Oil

| Component | Content (% by weight |
|---|---|
| Macrogol glycerol hydroxystearate | 6–8 |
| Eucalyptus oil/orange oil | 0.5–3.0 |
| Miglyol 812 | 50–60 |
| xanthan gum | 8–12 |
| lemon aroma | 0.05–0.2 |
| potassium sorbate | 0.1–0.2 |
| sodium saccharide | 0.04–0.08 |
| citric acid | 1.5–2.5 |
| aqua purificata | to 100% |

EXAMPLE 3

Since eucalyptus oil is known for its toxicological potential, the compatibility of Eucalyptus oil and of the inventive combinations of Eucalyptus oil and orange oil was investigated in an in vitro trial.

For this purpose, cultures of L-929 cells were treated with variable amounts (0.1–0.006 percent by volume of Eucalyptus oil by itself and of the inventive combination of Eucalyptus oil and orange oil and allowed to stand for forty-eight hours. At the end of this time, the number of live cells in the cultures, treated with the oils, was determined. The results obtained are summarized in Tables 1 and 2 and compared with the number of live cells in untreated cultures ("cell control").

TABLE

| Eucalyptus Oil | | | | | |
|---|---|---|---|---|---|
| Concentration | 0.0125% | 0.0100% | 0.0083% | 0.0071% | 0.0063% |
| Cells × $10^5$/mL | 1.025 | 1.108 | 1.848 | 1.267 | 2.388 |
| | 0.775 | 0.591 | 1.601 | 1.128 | 1.450 |
| | 0.906 | 0.516 | 1.208 | 1.317 | 1.075 |
| | 1.016 | 0.503 | 1.272 | 0.757 | 1.061 |
| Average | 0.931 | 0.680 | 1.482 | 1.117 | 1.494 |
| Standard Deviation | ±0.117 | ±0.288 | ±0.298 | ±0.253 | ±0.623 |
| Data as a percentage of the cell control of 2.38 × $10^5$/mL | 37.92% | 27.69% | 60.41% | 45.54% | 60.87% |

TABLE 2

| Eucalyptus Oil/orange oil Mixture | | | | | |
|---|---|---|---|---|---|
| Concentration | 0.1000% | 0.0500% | 0.0250% | 0.0167% | 0.0125% |
| Cells × $10^5$/mL | 1.137 | 2.410 | 3.597 | 3.017 | 5.345 |
| | 1.076 | 1.952 | 3.912 | 2.988 | 3.687 |
| | 1.431 | 2.483 | 3.562 | 3.941 | 4.077 |
| | 1.417 | 2.333 | 4.265 | 3.516 | 3.966 |
| Average | 1.315 | 2.295 | 3.834 | 3.366 | 4.269 |
| Standard Deviation | ±0.165 | ±0.236 | ±0.328 | ±0.454 | ±0.736 |
| Data as a percentage of the cell control of 2.38 × $10^5$/mL | 30.38% | 53.01% | 88.57% | 77.75% | 98.61% |

The Eucalyptus oil was tolerated only up to 0.008 percent (v/v) (Table 1). On the other and, the combination of the two oils was tolerated up to 0.02 percent (v/v) without cytotoxic effects (Table 2). This is indicated by a higher number of live cells. If corresponding concentrations are compared (0.0125 percent), 37.92 percent survive a Eucalyptus oil treatment and 98.6 percent survive the combined oil treatment. These results support the goods clinical compatibility, which has been observed.

What is claimed is:

1. A pharmaceutical composition for oral administration in the form of a hard or soft gelatin capsule comprising Eucalyptus oil and orange oil, wherein the ratio by weight of Eucalyptus oil to orange oil is between 1:10 and 10:1.

2. The pharmaceutical composition of claim 1, wherein the ratio by weight of Eucalyptus oil to orange oil is 2:1.

3. The pharmaceutical composition of claim 1, wherein the content of Eucalyptus oil and orange oil is 1 to 80 percent by weight.

4. The pharmaceutical composition of claim 1, wherein the content of Eucalyptus oil and orange oil is 10 to 75 percent by weight.

5. The pharmaceutical composition of claim 1, wherein the content of Eucalyptus oil and orange oil is 40 to 70 percent by weight.

6. The pharmaceutical composition of claim 1, or 3, wherein the composition further comprises at least one pharmaceutically acceptable inert ingredient.

7. A pharmaceutical composition for oral administration in the form of a liquid comprising Eucalyptus oil and orange oil, wherein the ratio by weight of Eucalyptus oil to orange oil is between 1:10 and 10:1.

8. The pharmaceutical composition of claim 7, wherein the ratio by weight of Eucalyptus oil to orange oil is 2:1.

9. The pharmaceutical composition of claim 7, wherein the content of Eucalyptus oil and orange oil is 0.1 to 10 percent by weight.

10. The pharmaceutical composition of claim 7, wherein the content of Eucalyptus oil and orange oil is 0.3 to 7 percent by weight.

11. The pharmaceutical composition of claim 7, wherein the content of Eucalyptus oil and orange oil is 0.5 to 3 percent by weight.

12. The pharmaceutical composition of claim 7, or 9, wherein the composition further comprises at least one pharmaceutically acceptable inert ingredient.

13. The pharmaceutical composition of claim 7, or 9, wherein the composition is a syrup.

\* \* \* \* \*